United States Patent
Bowlin et al.

(10) Patent No.: US 10,258,717 B2
(45) Date of Patent: Apr. 16, 2019

(54) COMPOSITIONS AND METHODS FOR ENHANCING HEALING AND REGENERATION OF BONE AND SOFT TISSUE

(71) Applicant: The University of Memphis, Memphis, TN (US)

(72) Inventors: Gary Lee Bowlin, Collierville, TN (US); Isaac Anthony Rodriguez, Memphis, TN (US); Brenton Walter Burger, Herndon, VA (US)

( * ) Notice: Subject to any disclaimer, the term of this patent is extended or adjusted under 35 U.S.C. 154(b) by 74 days.

(21) Appl. No.: 14/818,662

(22) Filed: Aug. 5, 2015

(65) Prior Publication Data
US 2016/0038646 A1 Feb. 11, 2016

Related U.S. Application Data

(60) Provisional application No. 62/033,599, filed on Aug. 5, 2014.

(51) Int. Cl.
| | |
|---|---|
| A61L 27/58 | (2006.01) |
| A61L 27/26 | (2006.01) |
| A61L 27/36 | (2006.01) |
| A61L 27/54 | (2006.01) |
| A61L 27/18 | (2006.01) |
| A61L 27/22 | (2006.01) |
| A61L 27/24 | (2006.01) |
| A61L 27/46 | (2006.01) |
| A61L 27/48 | (2006.01) |

(52) U.S. Cl.
CPC ............... *A61L 27/58* (2013.01); *A61L 27/18* (2013.01); *A61L 27/222* (2013.01); *A61L 27/24* (2013.01); *A61L 27/26* (2013.01); *A61L 27/3604* (2013.01); *A61L 27/365* (2013.01); *A61L 27/46* (2013.01); *A61L 27/48* (2013.01); *A61L 27/54* (2013.01); *A61L 2300/404* (2013.01); *A61L 2300/406* (2013.01); *A61L 2300/412* (2013.01); *A61L 2430/02* (2013.01)

(58) Field of Classification Search
CPC .. A61K 9/0014; A61K 38/39; A61K 2800/74; A61K 8/65; A61K 8/73; A61K 9/7023; A61Q 19/00; A61Q 17/005; A61Q 11/00; A01N 25/34; A61L 2300/404; A61L 15/28; A61L 15/44; A61L 26/0066; A61L 27/26; A61L 15/425; A61L 2300/41; A61L 2300/412; A61L 2300/414; A61L 26/0023; A61L 26/0033; A61L 27/56; A61L 15/325; A61L 2430/34; A61L 24/0015; A61L 24/0042; A61L 26/0038; A61L 26/0085; A61L 27/3633; A61F 13/0266; A61F 13/00012; A61F 13/00029; A61F 13/02; A61F 13/023; A61B 2017/00747; A61B 2017/00761
See application file for complete search history.

(56) References Cited

U.S. PATENT DOCUMENTS

| | | |
|---|---|---|
| 7,714,183 B2 | 5/2010 | Caskey |
| RE42,755 E | 9/2011 | Molan |
| 8,552,164 B2 | 10/2013 | Morganti et al. |
| 8,815,298 B2 | 8/2014 | Moloney |

FOREIGN PATENT DOCUMENTS

| | | | | |
|---|---|---|---|---|
| CN | 101879248 A | * | 11/2010 | |
| GB | 2484319 A | * | 6/2010 | ............. A61L 15/40 |
| JP | WO2010044042 A1 | * | 4/2010 | |
| WO | WO1993016657 | * | 9/1993 | ............... A61F 2/00 |

OTHER PUBLICATIONS

Da Silva et al. Honey: Chemical composition, stability and authenticity. Food Chemistry 196 (2016) 309-323.*
Wang et al. Hydrogel sheets of chitosan, honey and gelatin as burn wound dressings. Carbohydrate Polymers 88 (2012) 75-83.*
Neffe et al. Gelatin functionalization with tyrosine derived moieties to increase the interaction with hydroxyapatite fillers. Acta Biomaterialia 7 (2011): 1693-1701.*
Ferreira et al. Comparison of lyophilization, and freezing in honey as techniques to preserve cortical bone allografts used to repair experimental femoral defects in domestic adult cats. Arq. Bras. Med. Vet. Zootec., v.64, n. 2, p. 263-273, 2012.*
Rodriguez et al. A Preliminary Evaluation of Lyophilized Gelatin Sponges, Enhanced with Platelet-Rich Plasma, Hydroxyapatite and Chitin Whiskers for Bone Regeneration. Cells 2013, 2, 244-265.*
Barui et al. Honey based fibrous scaffold for tissue engineering application. Life Science Systems and Applications Workshop (LiSSA), 2011 IEEE/NIH (Apr. 7-8, 2011): 83-85.*
Nishikawa et al. Honeycomb Films of Biodegradable Polymers for Tissue Engineering. Mat. Res. Soc. Symp. Proc. 2002; vol. 724: 229-234.*
Beverly. What Is a Honey Comb Made of? http://honeyfanatic.com/author/beverly/.*
Mandal et al. Honey: its medicinal property and antibacterial activity. Asian Pac J Trop Biomed. Apr. 2011;1(2):154-60.*
Kim et al. Porous scaffolds of gelatin-hydroxyapatite nanocomposites obtained by biomimetic approach: characterization and antibiotic drug release. J Biomed Mater Res B Appl Biomater. Aug. 2005;74(2):686-98.*
Epperley et al. Manuka honey worked a miracle in healing the horse's horrific wound. Published: Nov. 28, 2012; pp. 1-5. http://www.veterinarypracticenews.com.*
Hillig et al. An open-pored gelatin/hydroxyapatite composite as a potential bone substitute. J Mater Sci: Mater Med (2008) 19:11-17.*
Manuka honey amounts converter. http://convert-to.com/654/active-manuka-honey-conversion-plus-nutritional-facts.html[Jul. 11, 2017 12:39:54 AM].*

(Continued)

*Primary Examiner* — Marcela M Cordero Garcia
*Assistant Examiner* — Jia-Hai Lee
(74) *Attorney, Agent, or Firm* — Bradley Arant Boult Cummings; Timothy L. Capria

(57) ABSTRACT

The invention features biodegradable materials, and in vitro and in vivo methods of using such compositions to promote bone and soft tissue growth and healing.

10 Claims, 13 Drawing Sheets

(56) References Cited

OTHER PUBLICATIONS

Sell et al. A Preliminary Study on the Potential of Manuka Honey and Platelet-Rich Plasma in Wound Healing. International Journal of Biomaterials vol. 2012, Article ID 313781. Hindawi Publishing Corporation. (Year: 2012).*

Zeng et al. Chitin Whiskers: An Overview. Biomacromolecules 2012, 13, 1-11. (Year: 2012).*

Liao et al. Hierarchically Biomimetic Bone Scaffold Materials: Nano-HA/Collagen/PLA Composite. J Biomed Mater Res Part B: Appl Biomater 69B: 158-165, 2004. (Year: 2004).*

Wang, T. et al., "Hydrogel sheets of chitosan, honey and gelatin as burn wound dressings", Carbohydrate Polymers, 2012, vol. 88, No. 1, pp. 75-83.

Rodriguez, I. A. et al., "A preliminary evaluation of lyohpilized gelatin sponges, enhanced with platelet-rich plasma, hydroxyapatite and chitin whiskers for bone regeneration", Cells, 2013, vol. 2, No. 2, pp. 244-265.

Junkasem, J. et al., "Fabrication of α-chitin whisker-reinforced poly (vinyl alcohol) nanocomposite nanofibers by electrospinning," Nanotechnology, 2006, vol. 17, No. 17, pp. 4519-4528.

Jayakumar, R. et al., "Novel chitin and chitosan nanofibers in biomedical applications", Biotechnology advances, 2010, vol. 28, No. 1, pp. 142-150.

Fetz, A. E. et al., "Compressed Electrospun Gelatin plus Chitin Whiskers plus Honey Membranes for Enhanced Periodontal Regeneration", 2014 TERMIS-AM Conference, Dec. 13, 2014, Tissue Engineering Part A, vol. 20, Supplement 1, pp. S135S136 (U-8).

* cited by examiner

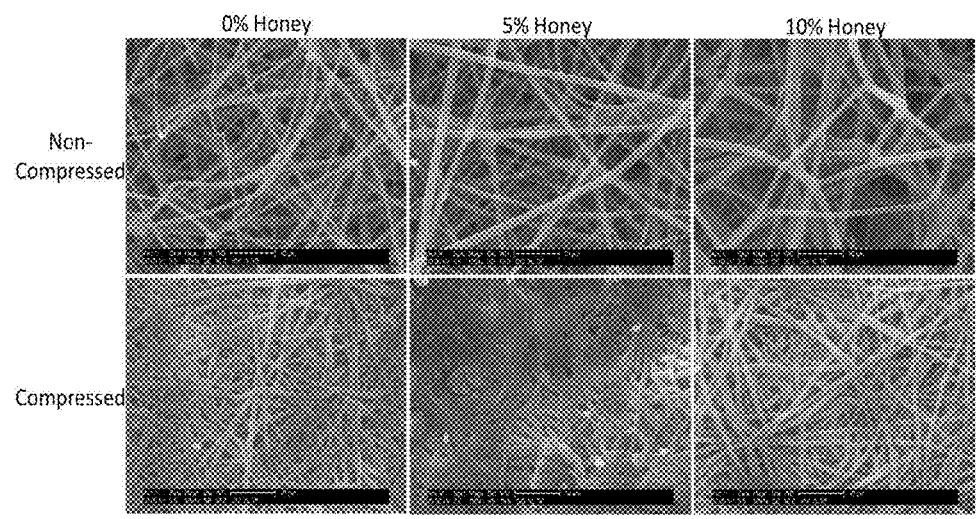
FIG. 1 SEM images of non-compressed and compressed electrospun gelatin + 15% CW + honey scaffolds (non-crosslinked). Scale bars and magnification at 10 μm and 2kx, respectively.

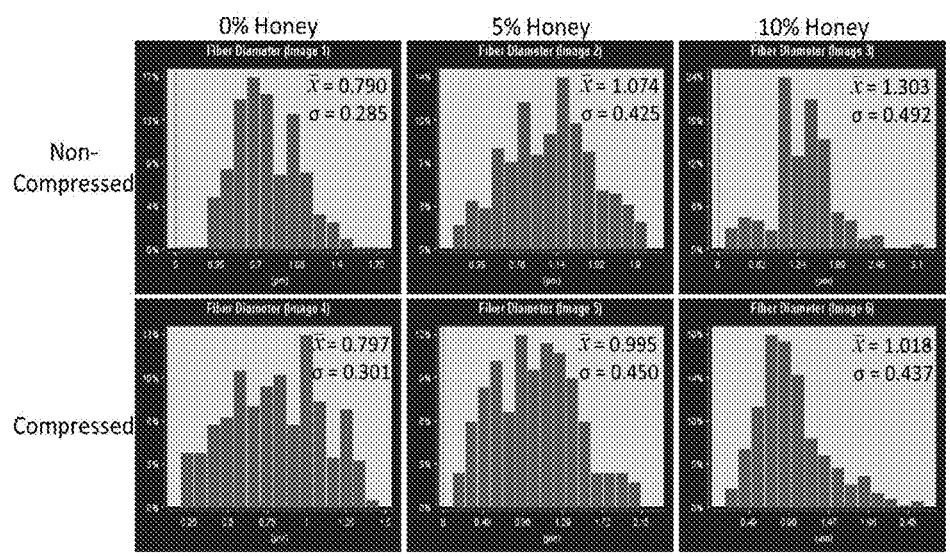
FIG. 2 FibraQuant™ automated fiber diameter analysis using SEM images from Figure 1. The above histograms show fiber size distribution along with the mean and standard deviations, in microns.

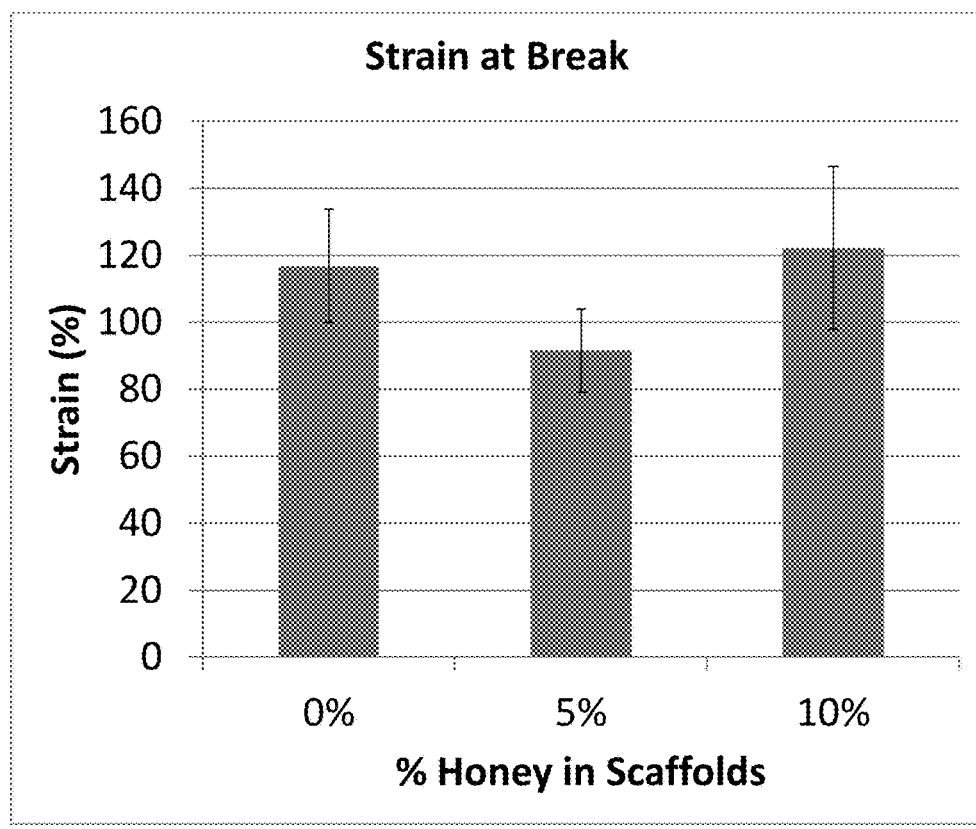
FIG 3A Uniaxial tensile testing of compressed electrospun membranes (strain at break).

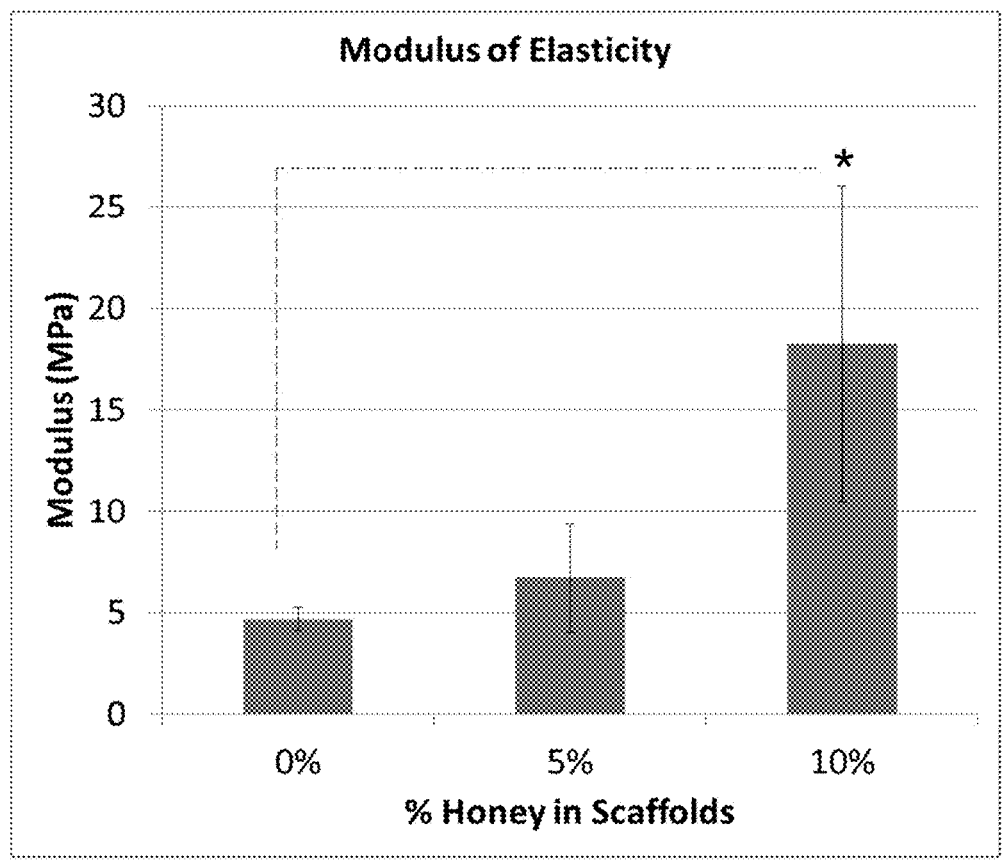
FIG 3B Uniaxial tensile testing of compressed electrospun membranes (elastic modulus).

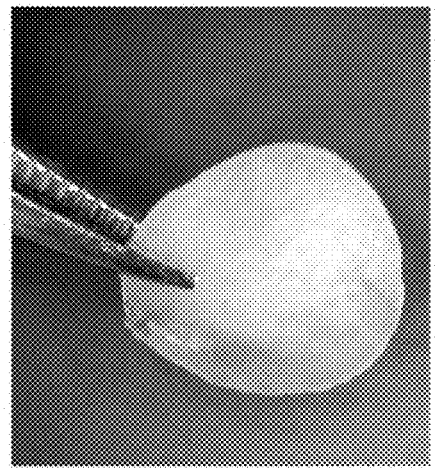
FIG. 4A Formable hydrated 10% honey compressed membranes.
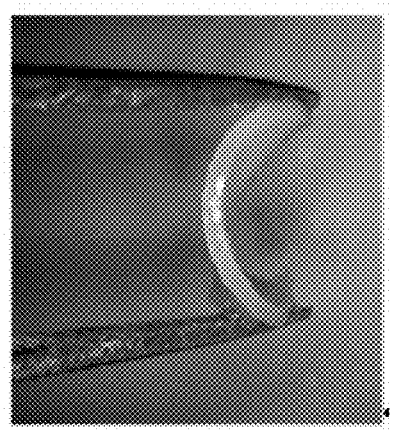
FIG. 4B Formable hydrated 10% honey compressed membranes.

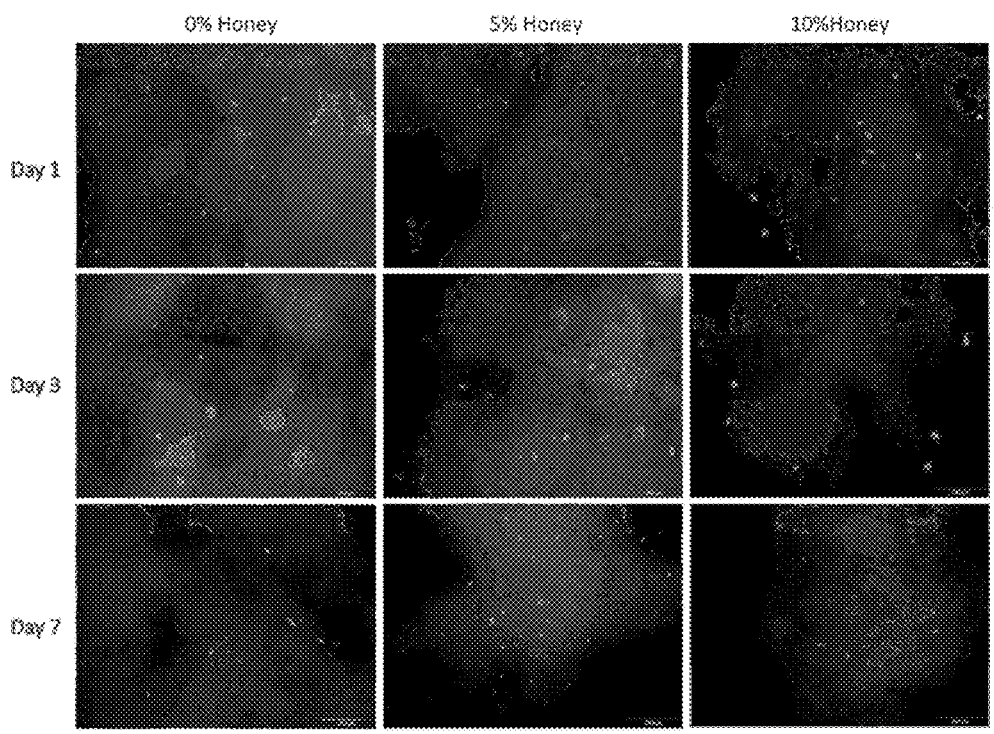
FIG. 5 DAPI images of cellularized (HDFs) compressed electrospun membranes. Scale bars and magnification at 200 μm and 10x, respectively.

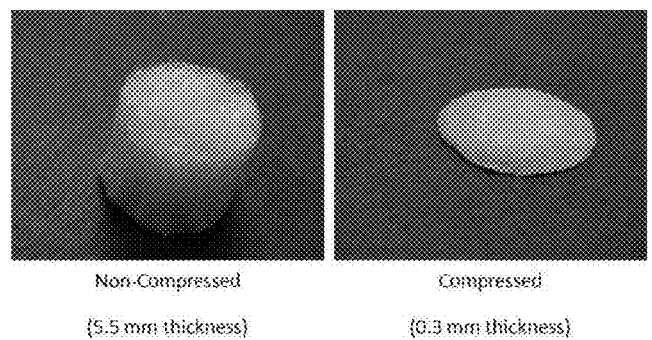

FIG. 6A DinoLite images of general gross appearance of non-compressed and compressed gelatin + 10%CW + 30 mg/mL Honey sponges. Sponges can be manufactured at any size (depending on the mold) and subsequently compressed.

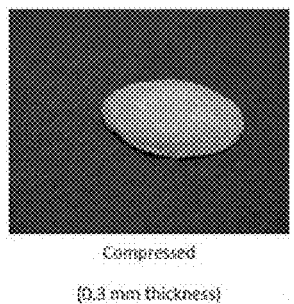

FIG. 6B DinoLite images of general gross appearance of non-compressed and compressed gelatin + 10%CW + 30 mg/mL Honey sponges. Sponges can be manufactured at any size (depending on the mold) and subsequently compressed.

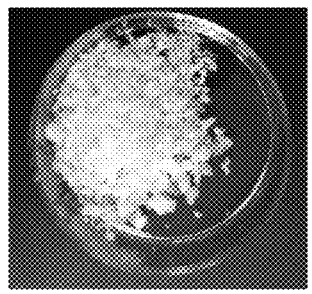
FIG. 7A Sponge particulate of varying sizes
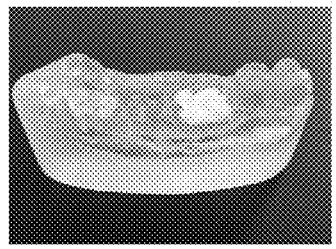
FIG. 7B Sponge particulate packed in a void (socket)
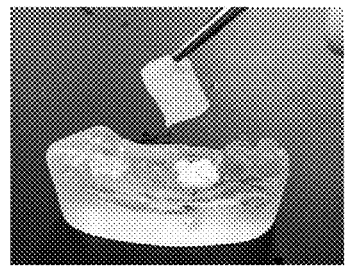
FIG. 7C Compressed lyophilized membrane being placed over socket filled with particulate

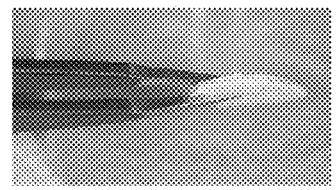
FIG.7D Dry lyophilized sponge compressed by hand
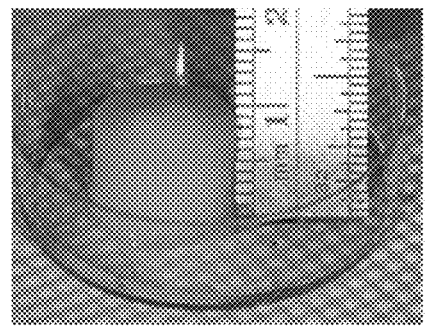
FIG.7E Swollen back to original size when hydrated

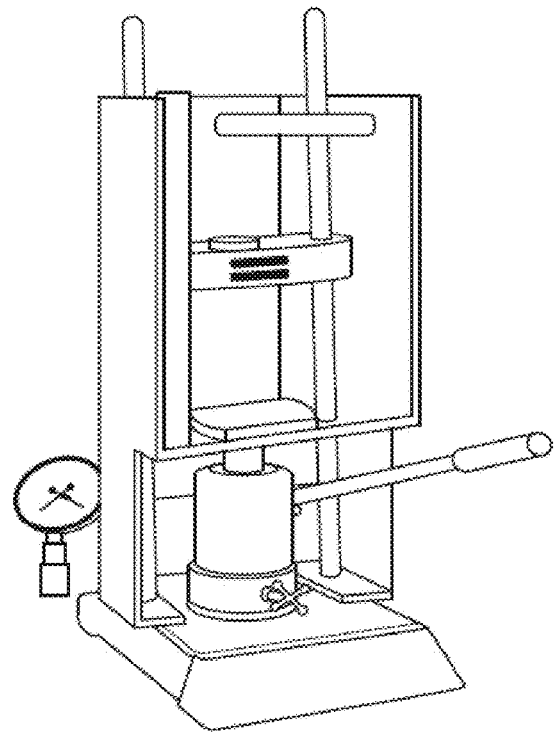
FIG. 8 Carver hydraulic unit used for scaffold compression.
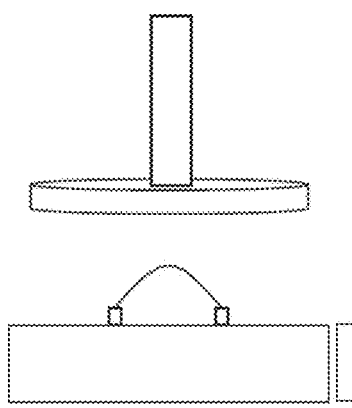
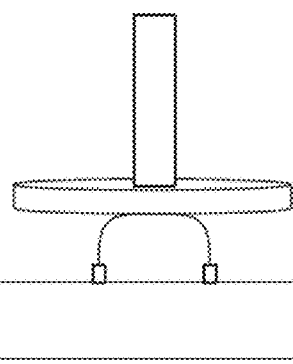
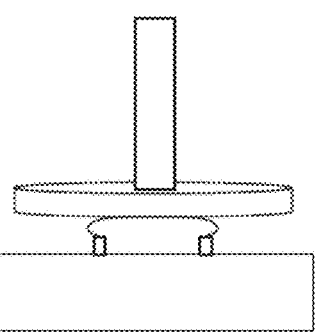
FIG. 9A          FIG. 9B          FIG. 9C

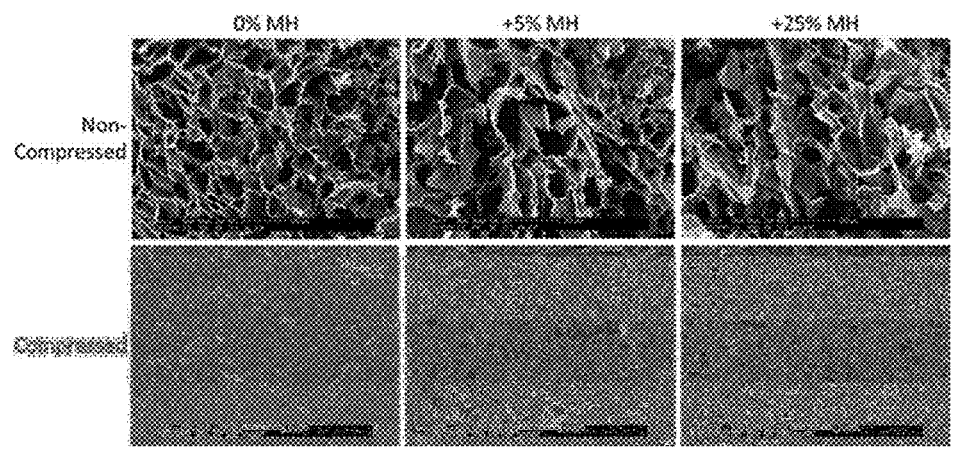
FIG. 10 SEM images of non-compressed and compressed gelatin + CW + MH membranes. Scale bars and magnification at 200 μm and 100x, respectively.

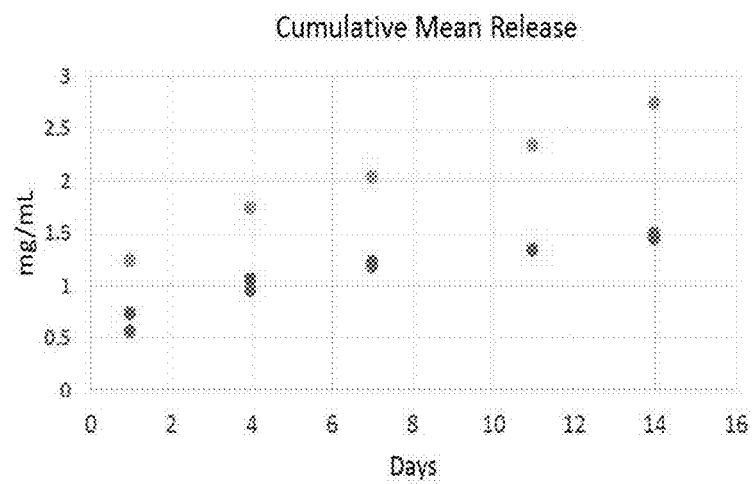
FIG. 11A Gelatin + CW + MH degradation results (BCA assay) as shown with cumulative mean release measurement
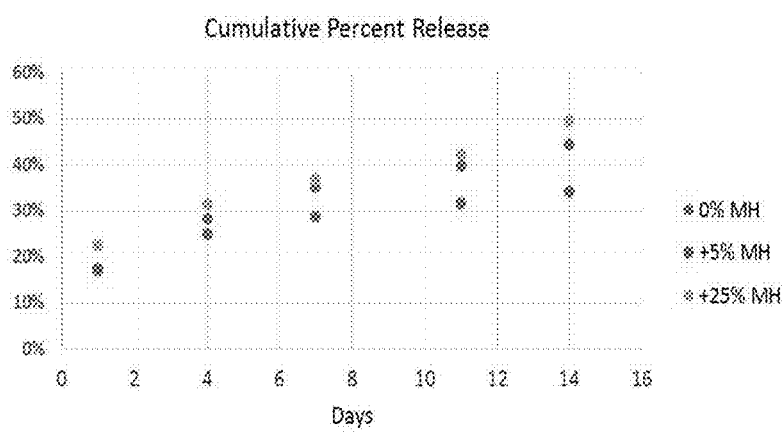
FIG. 11B Gelatin + CW + MH degradation results (BCA assay) as shown with cumulative percent release measurement

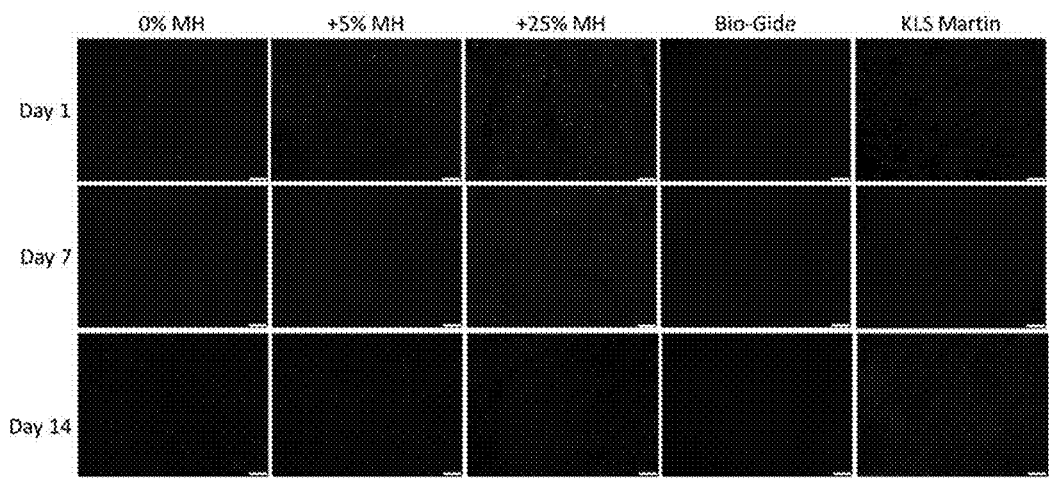
FIG. 12 DAPI images of cellularized (HDFs) compressed gelatin + CW + MH membranes. Scale bars and magnification at 100 μm and 10x, respectively.
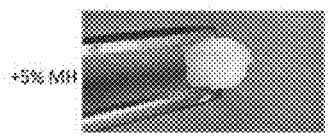
FIG. 13A Formable hydrated membranes.
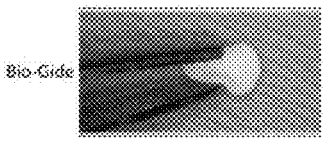
FIG. 13B Formable hydrated membranes.
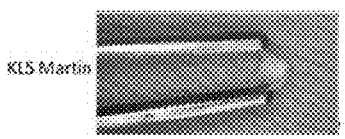
FIG. 13C Formable hydrated membranes.

COMPOSITIONS AND METHODS FOR ENHANCING HEALING AND REGENERATION OF BONE AND SOFT TISSUE

BACKGROUND OF THE INVENTION

Clinically, bone resorption in the maxillary and mandibular jaws occurs after loss of dentition. Partial edentulism affects 40% of the adult population and is estimated to increase in the next 15 years to more than 200 million individuals (*Facts and Figures*. 2012, American College of Prosthodontics). In such cases, the bone resorption causes the alveolar ridge to decrease in width and height with a 50% loss in bone width occurring during the first year after a tooth is lost, two-thirds of which occur in the initial 3 months (Schropp, L., et al., Int J Periodontics Restorative Dent, 2003. 23(4): p. 313-23). The result of this is that before the patient's dentition is restored with dental implants, a separate procedure is required to replace this lost bone structure. There are various surgical procedures available to graft the deficit alveolar ridge for both height and width. To do this a bone graft, commonly allograft bone powder/particulate or block is placed in the void space to provide osteoconductive/osteoinductive cues for targeted bone regeneration. Many of these procedures utilize a guided bone regenerative (GBR) membrane to maintain the bone graft in place as well as soft tissues. To date, the "ideal" GBR membrane for large defect, alveolar ridge bone grafting has yet to be developed (Bottino, M. C., et al., Dent Mater, 2012. 28(7): p. 703-21; Dimitriou, R., et al., BMC Med, 2012. 10: p. 81).

Current biomaterials used as membrane barriers in dental extractions are often difficult to handle, degrade quickly, and offer no enhanced wound regeneration which is paramount for complete and timely closure of the tissue over a bone graft. There is an urgent need for a biodegradable material that would support bone growth, promote bone and soft tissue healing, and inhibit infection. Such a material would be useful for treating injuries, conditions and disorders affecting bone and soft tissue.

SUMMARY OF THE INVENTION

As described herein, the present invention features biodegradable barrier materials and in vitro and in vivo methods of using such materials to promote bone and soft tissue growth and healing.

In one aspect, the invention provides a composition comprising:
a) a biodegradable polymer; and
b) a honey.

In certain embodiments, the composition additionally comprises c) a filler.

In certain embodiments, the biodegradable polymer comprises a protein. In certain embodiments, the protein is gelatin. In certain embodiments, the protein is collagen.

In certain embodiments, the biodegradable polymer comprises poly(lactic acid).

In certain embodiments, the honey is present in an amount of about 1 part to about 300 parts by weight relative to 100 parts by weight of the biodegradable polymer, e.g. gelatin. In certain embodiments, the honey is present in an amount of about 1 part to about 100 parts by weight, of about 1 part to about 50 parts by weight, of about 1 part to about 15 parts by weight, or particularly of about 5 part to about 10 parts by weight relative to 100 parts by weight of the biodegradable polymer, e.g. gelatin.

In certain embodiments, the filler is present in an amount of 1-300 parts by weight relative to 100 parts by weight of the biodegradable polymer. Preferably, the filler is present in an amount of about 1-100 parts by weight, 5-50 parts by weight or particularly 10-20 parts by weight.

In certain embodiments, the filler comprises a nanofiller, a microfiller or mixtures thereof. The nanofiller has an average diameter in nanoscale ranging from about 1 nm to about 999 nm, or less than about 1 μm. In certain embodiments, the nanofiller suitably has an average diameter less than about 990 nm, less than about 900 nm, less than about 800 nm, less than about 700 nm, less than about 600 nm, less than about 500 nm, less than about 400 nm, less than about 300 nm, less than about 200 nm, or less than about 100 nm. In certain embodiments, the nanofiller suitably has an average diameter of about 1-100 nm, of about 10-80 nm, of about 25-75 nm, or particularly of about 50 nm. The microfiller is a micron-sized filler having an average diameter in microscale at least about 1 μm. The microfiller suitably has an average diameter of about less than about 10 μm, less than about 9 μm, less than about 8 μm, less than about 7 μm, less than about 6 μm, less than about 5 μm, less than about 4 μm, less than about 3 μm, less than about 2 μm, or particularly of about 1-2 μm.

In certain embodiments, the filler comprises chitin whiskers. In certain embodiments, the filler comprises hydroxyapatite. In certain embodiments, the filler (such as chitin whiskers) are present in an amount of about 15 parts by weight relative to 100 parts by weight of the biodegradable polymer. In certain embodiments, the chitin whiskers have an average diameter of about 25-75 nm, or particularly an average diameter of about 50 nm. In certain embodiments, the chitin whiskers have an average length of about 200-400 nm, of about 250-300 nm, or particularly of about 280 nm.

In certain embodiments, the composition further comprises at least one or more additional filler or at least one or more therapeutic agents, such as antibiotic. In certain embodiment, the therapeutic agent is a therapeutically effective amount of honey. In particular embodiments, the composition further comprises an antibacterially-effective amount of honey, which ranges from about 50 parts to about 300 parts, or from about 100 parts to about 200 parts by weight relative to 100 parts by weight of the biodegradable polymer. In particular embodiment, the composition further comprises an effective amount of honey for stimulating or enhancing regeneration (cell proliferation and migration), which ranges from about 10 parts to about 100 parts, from about 20 parts to about 70 parts by weight, or particularly of about 50 part by weight relative to 100 parts by weight of the biodegradable polymer. The honey for therapeutic use is same to or different from the above described honey.

In another aspect, the invention provides a membrane comprising:
a) a biodegradable polymer;
b) a honey.

In certain embodiments, the membrane may additionally comprise a filler.

In another aspect, the multiple-layer membrane comprising at least two layers of a membrane of the invention.

In certain embodiments, the multiple-layer membrane comprises 2-4 layers of the membrane of the invention. In certain embodiments, the multiple-layer membrane comprises four layers of the membrane. In certain embodiments, the at least two layers are crosslinked. In certain embodiments, the at least two layers are crosslinked with 1-ethyl-3-(3-dimethylaminopropyl)carbodiimide, genipin, glutaraldehyde or mixture thereof.

In another aspect, the invention provides a method of making a composition of the invention (i.e., a composition comprising a biodegradable polymer and a honey. The composition may additionally include a filler. The method comprises: forming a composition by combining the biodegradable polymer and honey with a solvent.

Preferably, the method comprises:
a) dispersing the filler in a solvent to form a dispersion; and
b) combining the biodegradable polymer and honey with the dispersion to form the composition.

In certain embodiments, the solvent is 2,2,2-trifluoroethanol, 1,1,1,3,3,3-hexafluoro-2-propanol (HFP) or 9:1 acetic acid:water. In certain embodiments, the solvent does not significantly solubilize the honey under the conditions used to form and process the composition, fiber, and/or membrane.

In another aspect, the invention provides a fiber comprising:
a) a biodegradable polymer; and
b) a honey.

The fiber may further comprise a filler.

In a preferred aspect, the "fiber" may include a nanofiber, a microfiber, or a nano-microfiber. The fiber may be formed in a bundle without limitation to the number or the total thickness thereof, comprising the nanofiber, the microfiber, the nano-microfiber or mixture thereof. In certain embodiments, the nanofiber has an average diameter or thickness in nanoscale ranging from about 1 nm to about 950 nm. Preferably, the nanofiber suitably has an average diameter or a thickness less than about 100 nm. The microfiber has an average diameter or thickness in microscale ranging from about 1 μm to about 950 μm. Preferably, the microfiber suitably has an average diameter or a thickness of about less than about 10 μm. Further, the nano-microfiber suitably has an average diameter or thickness ranging from about 100 nm to about 10 μm.

In another aspect, the invention provides a method of making a fiber comprising: a biodegradable polymer and a honey. The fiber may additionally comprise a filler. The method comprises:
forming a composition by combining the biodegradable polymer and honey with a solvent; and
electrospinning the composition to form the fiber.

Preferably, the method comprises:
a) dispersing the filler in a solvent to form a dispersion;
b) combining the biodegradable polymer and honey with the dispersion to form a composition; and
c) electrospinning the composition to form the fiber.

In another aspect, the invention provides a method of making a membrane comprising: a biodegradable polymer and a honey. The membrane may additionally comprise a filler. The method comprises:
forming a composition by combining the biodegradable polymer and honey with a solvent; and
electrospinning the composition to form fibers, thereby forming the membrane.

Preferably, the method comprises:
a) dispersing the filler in a solvent to form a dispersion;
b) combining the biodegradable polymer and honey with the dispersion to form a composition; and
c) electrospinning the composition to form fibers, thereby forming the membrane.

In another aspect, the invention provides a method of making a membrane of the invention, the method comprising:
a) dispersing the filler in a solvent to form a dispersion;
b) combining the biodegradable polymer and honey with the dispersion;
c) removing solvent from the dispersion to form a sponge; and
d) compressing the sponge to form the membrane.

In certain embodiments, the step of compressing comprises compressing the sponge at a pressure of at least 3000 pounds.

In certain embodiments, the membrane is further processed to form a block, a particulate, swelling membrane, non-compressed membrane or compressed membrane.

In another aspect, the invention provides a multiple-layer membrane comprising:
a) a biodegradable polymer; and
b) a honey.

The multiple-layer membrane may further comprise a filler.

In another aspect, the invention provides a method of making a multiple-layer membrane of the invention, the method comprising:
forming a composition by combining the biodegradable polymer and honey with a solvent;
electrospinning the composition to form fibers;
collecting the fibers to form at least two non-woven mesh membranes; and
attaching the at least two non-woven mesh membranes to form the multiple-layer membrane.

Preferably, the method comprises:
a) dispersing the filler in a solvent to form a dispersion;
b) combining the biodegradable polymer and honey with the dispersion;
c) electro spinning the composition to form fibers;
d) collecting the fibers to form at least two non-woven mesh membranes; and
e) attaching the at least two non-woven mesh membranes to form the multiple-layer membrane.

The multi-layer membrane may be compressed or may not be compressed.

In another aspect, the invention provides a method of promoting bone regeneration, the method comprising contacting a bone surface with a composition, fiber, compressed membrane, particulate, swelling membrane, non-compressed membrane, or multiple-layer membrane (compressed or non-compressed) of the invention.

In another aspect, the invention provides a method of promoting healing of a bone defect, the method comprising contacting the bone defect with a composition, fiber, compressed membrane, particulate, swelling membrane, non-compressed membrane, or multiple-layer membrane (compressed or non-compressed) of the invention.

In another aspect, the invention provides a method of preventing infection of a bone defect, the method comprising contacting the bone defect In another aspect, with a composition, fiber, compressed membrane, particulate, swelling membrane, non-compressed membrane, or multiple-layer membrane (compressed or non-compressed) of the invention.

In another aspect, the invention provides a method of promoting soft tissue healing in a damaged tissue, the method comprising contacting the damaged tissue with a composition, fiber, compressed membrane, particulate, swelling membrane, non-compressed membrane, or multiple-layer membrane (compressed or non-compressed) of the invention.

In another aspect, the invention provides a method of promoting a macrophage response in a tissue, the method comprising contacting the tissue with a composition, fiber, compressed membrane, particulate, swelling membrane, non-compressed membrane, or multiple-layer membrane (compressed or non-compressed) of the invention.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) as detected by standard art known methods such as those described herein. As used herein, an alteration includes a 10%, 25%, 40%, 50% or greater change.

By "soft tissue disease or injury" is meant any disease, disorder, or trauma that disrupts the normal function or connectivity of a soft tissue or tissues.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ, including bone.

By "effective amount" or "therapeutically effective amount" is meant the amount of a composition of the invention required to provide desired effect or release the symptoms of a disease relative to an untreated subject. The effective amount of a cellular composition used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "therapeutically effective" amount. "Engraft" refers to the process of cellular contact and incorporation into an existing tissue of interest (e.g., bone or soft tissue) in vivo.

By "enhancing bone healing" is meant increasing the extent of bone growth or healing relative to a control condition. Preferably the increase is by at least 2-fold, 2.5-fold, 3-fold or more.

By "microscale" is meant between 100 nm and 999 µm in size. A particle that is microscale is larger in size than a nanotube.

As used herein, "obtaining" as in "obtaining an agent" includes synthesizing, purchasing, or otherwise acquiring the agent.

By "reference" is meant a standard or control condition.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 shows SEM images of non-compressed and compressed electrospun gelatin+15% CW+honey scaffolds (non-crosslinked). Scale bars and magnification at 10 µm and 2kx, respectively.

FIG. 2 shows FibraQuant™ automated fiber diameter analysis using SEM images from FIG. 1. The above histograms show fiber size distribution along with the mean and standard deviations, in microns.

FIGS. 3A-3B show the results of uniaxial tensile testing of compressed electrospun membranes: A. Strain at break, B. elastic modulus.

FIGS. 4A-4B show exemplary formable hydrated 10% honey compressed membranes.

FIG. 5 shows DAPI images of cellularized (HDFs) compressed electrospun membranes. Scale bars and magnification at 200 µm and 10×, respectively.

FIGS. 6A-6B show DinoLite images of general gross appearance of non-compressed and compressed gelatin+10% CW+30 mg/mL honey sponges.

FIG. 7A shows an exemplary membrane (sponge) particulate of various sizes.

FIG. 7B shows an exemplary sponge particular packed in a void (socket).

FIG. 7C shows an exemplary use of the particulate that is covered by the compressed lyophilized membrane, when the particulate is packed in a void.

FIG. 7D shows an exemplary dry lyophilized sponge compressed by hand.

FIG. 7E shows an exemplary swollen back to original size when hydrated.

FIG. 8 shows a Carver hydraulic unit used for scaffold compression.

FIGS. 9A-9C schematically illustrates steps of an exemplary mechanical testing method.

FIG. 10 shows SEM images of non-compressed and compressed gelatin+CW+MH membranes, which includes scale bars and magnification at 200 μm and 100×, respectively.

FIG. 11A shows a graph including Gelatin+CW+MH degradation results (BCA assay) as shown with cumulative mean release measurement.

FIG. 11B shows a graph including Gelatin+CW+MH degradation results (BCA assay) as shown with cumulative percent release measurement.

FIG. 12 shows DAPI images of cellularized (HDFs) compressed gelatin+CW+MH membranes. Scale bars and magnification at 100 μm and 10×, respectively.

FIGS. 13A-13C show exemplary formable hydrated membranes.

DETAILED DESCRIPTION OF THE INVENTION

The present invention features biodegradable polymer-based materials or matrices (e.g., fibers or membranes) comprising honey; and in vitro and in vivo methods of using such compositions to ameliorate an injury or condition (e.g., bone injury or trauma associated with dental surgery).

The invention is based, at least in part, on the discovery that biodegradable membranes comprising honey can support and promote bone and tissue growth and regeneration. In addition, the biodegradable membranes include an antibacterially-effective amount of honey, thereby providing an antibacterial barrier against infection and promoting a sterile environment for wound healing.

Scaffolds

In general, the materials of the invention comprise a biodegradable polymerand a honey (e.g., an antibacterial, bactericidal, and/or wound healing amount of honey). Preferably, the materials may additionally comprise a filler.

A variety of biodegradable polymers are known in the art. Preferred biodegradable polymers include proteins (such as gelatin and collagen), polymers derived from naturally-occurring monomers (such as poly(lactic acid (PLA)), and polymers derived from synthetic monomers (such as polydioxanone (PDO)). Desirably, biodegradable materials will degrade over a time period of less than a year, more preferably less than six months. In general, any biodegradable polymer that is biocompatible, and can be shaped or formed into fibers and membranes, can be employed in the present materials. Copolymers or mixtures/blends (multi-component) of biodegradable polymers can also be employed.

Other biocompatible polymers, some of which are biodegradable, include, e.g., Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly (ethylene glycol), poly(methacrylic acid), polylactic acid (PLA), polyglycolic acids (PGA), poly(lactide-co-glycolides) (PLGA), nylons, polyamides, polyanhydrides, poly (ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Some preferred synthetic matrix materials include PEA, PGA, copolymers of PLA and PGA, polycaprolactone, poly(ethylene-co-vinyl acetate), (EVOH), PVA, and PEO, See also U.S. Pat. No. 7,374,774 (which is incorporated herein by reference).

The term "filler", as used herein, refers to an organic or inorganic biocompatible material that provides structural reinforcement or rigidity to a polymer fiber, filament, or membrane. The filler may be a crystalline, a fiber, or a particle. Alternatively, the filler suitably has a shape of rod, fiber, sphere, oval, polyhedral crystal, and the like, however, the shape of the filler is not particularly limited thereto. The filler has an average diameter in nanoscale (nanofiller) ranging from about 1 nm to about 950 nm. The nanofiller suitably has an average diameter of about 1-100 nm, of about 10-80 nm, of about 25-75 nm, or particularly of about 50 nm. Alternatively, the filler has an average diameter in microscale (microfiller) that is greater than at least about 100 nm. The microfiller suitably has an average diameter of about less than about 10 μm, less than about 9 μm, less than about 8 μm, less than about 7 μm, less than about 6 μm, less than about 5 μm, less than about 4 μm, less than about 3 μm, less than about 2 μm, or particularly less than about 1 μm. For example, the filler is a nanocrystalline or fiber material and has an average diameter or thickness of less than about 100 nm, and advantageously may have an average length of less than about 500 nm. Advantageously, a nanofiller can possess an electrostatic charge, which may adhere to or attract growth factors when implanted or applied to a wound site. Examples of nanofiller materials suitable for use in the present materials include chitin whiskers and hydroxyapatite nanocrystals. Mixtures of fillers comprising nanofillers and microfillers can also be used without limitation.

The materials of the invention further comprise honey. Any type of honey can be used. Examples of types of honey include Manuka honey, Leptospermum Honey or buckwheat honey. Mixtures of different honeys can also be employed. For example, Manuka honey is an active or a therapeutic Manuka honey that has a UMF rating above 10. The honey is present in the compositions and materials of the invention in an amount effect to inhibit the growth or spread of bacteria, such as pathogenic bacteria. Exemplary bacteria include *S. aureus*, (including methacillin-resistant *S. aureus* (MRSA)), *P. gingivalis*, *S. epidermidis*, *Enterococcus faecium*, *E. coli*, *P. aeruginosa*, *E. cloacae*, and *Klebsiella oxytoca*. In addition, the buckwheat honey can be included in an effective amount for healing.

The amount of honey to be used depends in part on the nature of the wound or injury to be treated with a composition of the invention; the type of bacterium to be inhibited; the concentration of the honey; and the antibacterial properties of the particular honey employed. The antibacterial, antimicrobial, and bactericidal properties of honey are dependent on various factors including the concentration of methylglyoxal (MGO), Unique Manuka Factor (UMF), the presence of additional phenolic compounds in the honey, wound pH, pH of the honey, and osmotic pressure exerted by the honey. One of ordinary skill in the art will be able to select a suitable type and amount of honey for use in the present compositions using no more than routine experimentation. In certain embodiments, the amount of honey is 1 part to 15 parts by weight (1-15 weight percent) based on the weight amount of the biodegradable polymer.

In preferred embodiments, a composition of the invention include 100 parts by weight of a biodegradable polymer, and about 1 part to about 15 parts by weight of honey. The composition may additionally comprise 10-20 parts by weight of filler. Additional compounds or agents can also be present as described herein.

In preferred embodiments, the composition further comprises a therapeutically effective amount of honey. For example, honey in an antibacterially-effective amount is added to the composition, which ranges from about 50 parts to about 300 parts, or from about 100 parts to about 200 parts by weight relative to 100 parts by weight of the biodegradable polymer. In addition, additional amount of honey is added to the composition to stimulate or enhancing regeneration (cell proliferation and migration), which ranges from about 10 parts to about 100 parts, from about 20 parts to about 70 parts by weight, or particularly of about 50 part by weight relative to 100 parts by weight of the biodegradable polymer.

Methods for Preparing Compositions

Compositions comprising a biodegradable polymer, a filler, and a honey can be prepared by any suitable method, some of which are known in the art. In general, a filler can be suspended or dispersed in a solvent (which will not substantially dissolve the filler) to form a dispersion or suspension; the biodegradable polymer and the honey are then mixed with the dispersion or suspension to form a composition of the invention. In certain embodiment, a therapeutically effective amount of honey is additionally added to the composition for antibacterial effect or enhancing regeneration. In certain embodiments, the solvent is 2,2,2-trifluoroethanol, 1,1,1,3,3,3-hexafluoro-2-propanol (HFP) or 9:1 acetic acid:water. The amount of solvent used should be minimized to facilitate electrospinning or other processing of the composition into fibers and membranes.

Methods for Preparing Fibers and Membranes

A composition comprising a biodegradable polymer, a filler, and an antibacterially-effective amount of honey can be used to prepare fibers and membranes by any suitable method, some of which are known in the art. In one embodiment, a fiber or membrane is formed by electrospinning Electrospinning is a known technique (see, e.g., Li et al., Biomaterials. 2005 October; 26(30):5999-6008.) and electrospinning apparatus can be purchased commercially. For example, a charged solution comprising, for example, a biodegradable polymer is fed through a small opening or nozzle (usually a needle or pipette tip). Due to its charge, the solution is drawn toward a grounded collecting plate, e.g., a metal screen, plate, or rotating mandrel, typically 5-30 cm away, as a jet. During the jet's travel, the solvent gradually evaporates, and a charged fiber is left to accumulate on the grounded target. The charge on the fibers eventually dissipates into the surrounding environment. If the target is allowed to move with respect to the nozzle position, specific fiber orientations (aligned or random) can be achieved.

The compositions of the invention can be made as electrospun fiber compositions.

In one embodiment, the invention provides a method of producing a membrane, the method comprising:

a) dispersing a filler in a solvent to form a dispersion;
b) combining a biodegradable polymer and honey with the dispersion to form a composition; and c) electrospinning the composition to form fibers, thereby forming a membrane comprising a biodegradable polymer, a filler, and an antibacterially-effective amount of honey.

In certain embodiments, the filler is added to the composition, such that the step a) can be omitted and the biodegradable polymer and honey can be combined with the solvent to form a composition.

The method may further comprise adding at least one additional filler, at least one therapeutic agent, or a therapeutically effective amount of honey to the composition before electrospinning. The electrospun membrane can be formed in multiple layers. For example, the composition can be additionally electrospun on top of one layer or other layers to create multiple-layer electrospun membrane.

In another embodiment, the solvent can be removed from a dispersion comprising a biodegradable polymer, a filler, and an antibacterially-effective amount of honey to form a sponge. Solvent can be removed by evaporation or lyophilization (freeze-drying). Thus, in one embodiment, the invention provides a method of producing a membrane, the method comprising:

a) dispersing a filler in a solvent to form a dispersion;
b) combining a biodegradable polymer and honey with the dispersion;
c) removing solvent from the dispersion to form a sponge; and
d) compressing the sponge to form a membrane comprising a biodegradable polymer, a filler, and an antibacterially-effective amount of honey.

In certain embodiments, the filler is added to the composition, such that the step a) can be omitted and the biodegradable polymer and honey can be combined with the solvent to form a composition.

The method may further comprise adding at least one additional filler, at least one therapeutic agent, or a therapeutically effective amount of honey to the composition.

It will be appreciated from context that the term "membrane" is used herein to refer to a product after compression of either electrospun mats/membranes or compression of a sponge, as described herein. Thus, the "membranes" herein include both compressed fibers and compressed sponge (unless otherwise clear from context).

The sponge can be lyophilized before compressing.

In certain embodiments, the sponge (lyophilized or non-lyophilized) can be suitably processed in a block or a particulate or ground form before compressing, for example, based on applications thereof depending on the bone grafting application.

Alternatively, the compressed sponge, fibers or membrane can be suitably processed in a block or a particulate or ground form after compressing depending on the bone grafting application.

Alternatively, the sponge is not compressed, or compressed with less pressure or substantially less pressure, e.g. by hand, only to give swelling potential (FIGS. 7D-7E).

The multiple-layer membrane can be formed by attaching the at least two membranes.

In certain embodiments, the multiple-layer membrane is formed by compressing multiple layers of sponges. In particular embodiment, the multiple-layer membrane is formed from multiple lyophilized sponges by compressing multiple layers thereof. The multiple-layer membrane can be compressed or not be compressed. For example, the multiple-layer membranes can be formed by compressing multiple layers of membranes formed by any of the methods described herein. In general, compression of 2-10 membranes (more preferably 2-4 membranes) between two surfaces (such as stainless steel plates or blocks, e.g., in a hydraulic press) at a pressure of 4,000-24,000 pounds will generally result in compression bonding of the membranes to form a multiple-layer membrane.

Alternatively, the multiple-layer membrane can be formed using multiple solvents. In certain embodiments, at least two or more of solvents having difference densities are used to dissolve the fillers and to combine other components (e.g. biodegradable polymer and honey). For example, solutions made from the composition and different solvents are combined, and the combined solutions may form distinct layers based on the densities of the solvents. After removing the solvents, multiple-layered sponges and multiple-layered membrane can be prepared. The multiple-layer membrane may be compressed or may not be compressed.

The membranes can be cross-linked using cross-linking reagents. Thus, in certain embodiments, the invention provides multiple-layer membranes having at least two layers, wherein the at least two layers are crosslinked, for example, to stabilize multiple-layered membrane structure. Exemplary cross-linking reagents include 1-ethyl-3-(3-dimethylaminopropyl) carbodiimide (or other carbodiimides), genipin, or glutaraldehyde. The membranes can be immersed in a solution of the cross-linking agent (e.g., 20-40 mM) in a solvent such as ethanol. When the desired amount of cross-linking has occurred, the membranes can be removed from the solution and rinsed before use.

A membrane for use in the therapeutic methods of the invention should have sufficient rigidity to support the surrounding soft tissue, be malleable at its glass transition temperature (Tg) but regain rigidity on cooling (i.e. hold shape formed in situ), and be biocompatible in that it will promote osseointegration and not adversely affect the surrounding soft tissue. The membrane should resorb within 6-9 months as it takes approximately 6 months for allograft bone to consolidate into new bone in the mandible and maxilla bone graft surgeries. The membranes of the invention are flexible, moldable upon heating, maintain their shape upon cooling, are less acidic during degradation, and the fibrous architecture will regulate the macrophage (MAC) response and allow for regeneration of bone and tissue (M2 MAC phenotype) versus the inflammatory (M1 MAC phenotype).

The size and thickness of a membrane of the invention can be varied according to the intended use. The membranes can be spun to a desired size, or a sponge can be cast to a desired size, followed by compression to a desired density and thickness. For example, barrier membranes are commonly between 0.1-0.4 mm in thickness, so the sponge can be suitably compressed to a thickness of about 0.1-0.4 mm.

The membrane can have any shape (round, square, rectangular, irregular). In exemplary embodiments, a membrane of the invention has a width from 1 to 20 mm and a length from 1 to 20 mm. In certain embodiments, a membrane is less than 1 mm in thickness, less than 0.5 mm thickness, less than 0.3 mm in thickness, or less than 100 microns in thickness.

In certain embodiments, a membrane of the invention has a strain at break of at least 90%, 100%, 110% or 120%. In certain embodiments, a membrane of the invention has modulus of elasticity of at least about 5 mPa, or 10, 15, 20, or 25 mPa. In certain embodiments, a membrane of the invention has a maximum compression load of at least about 0.26N.

Therapeutic and Prophylactic Applications

The present invention provides a ready supply of materials useful for ameliorating conditions associated with bone or soft tissue disease or injury. Compositions and materials of the invention are administered (e.g., directly or indirectly) to a damaged or diseased tissue or organ where they engraft and establish functional connections with a target tissue (e.g., bone, muscle, gum, gingiva, mucous membrane, skin). In one embodiment, a membrane of the invention enhances bone healing. Methods for repairing damaged tissue or organs may be carried out either in vitro, in vivo, or ex vivo. In a particular embodiment, the membrane is used in a dental application, e.g., in mandible and maxilla bone graft surgery.

In another embodiment, the invention provides a method of promoting bone regeneration, the method comprising contacting a bone surface with a composition, fiber, compressed membrane, particulate, swelling membrane, non-compressed membrane or multiple-layer membrane (compressed or non-compressed) of the invention. In certain embodiments, the method is a method of promoting bone regeneration after a surgical procedure on bone, including socket preservation, ridge augmentation, sinus grafting or bone grafting.

In another embodiment, the invention provides a method of promoting healing of a bone defect, the method comprising contacting the bone defect with a composition, fiber, compressed membrane, particulate, swelling membrane, non-compressed membrane or multiple-layer membrane (compressed or non-compressed) of the invention.

In another embodiment, the invention provides a method of preventing infection of a bone defect, the method comprising contacting the bone defect with a composition, fiber, membrane, particulate, swelling membrane, non-compressed membrane or multiple-layer membrane (compressed or non-compressed) of the invention.

In still another embodiment, the invention provides a method of promoting soft tissue healing in a damaged tissue, the method comprising contacting the damaged tissue with a composition, fiber, membrane, particulate, swelling membrane, non-compressed membrane or multiple-layer membrane (compressed or non-compressed) of the invention.

In certain embodiments of the above aspects, the method is a method of promoting bone regeneration after a surgical procedure on bone, including socket preservation, ridge augmentation, sinus grafting or bone grafting.

In yet another embodiment, the invention provides a method of promoting a macrophage response in a tissue, the method comprising contacting the tissue with a composition, fiber, membrane, particulate, swelling membrane, non-compressed membrane or multiple-layer membrane (compressed or non-compressed) of the invention.

Administration

Compositions, fiber, and membranes of the invention can be provided directly to a tissue or organ of interest (e.g., by direct application to a bone or tissue surface, or by surgical implantation). A membrane can be applied to cover, surround, fill, or otherwise contact a bone or tissue defect, wound, skin/wound healing, gingival recession or surgical site. If desired, expansion and differentiation agents can be provided prior to, during or after administration of the composition, fiber, or membrane to increase, maintain, or enhance production or differentiation of cells in vivo, including bone cells from a subject's bone or from any type of bone graft material/transplant, i.e., allogenic, xenogenic, alloplastic or genetically produced bone. Compositions of the invention include pharmaceutical compositions. When administering a therapeutic composition or material of the present invention (e.g., a pharmaceutical composition), it will generally be formulated in a unit dosage form. Additional therapeutic agents can be applied to the fibers or incorporated within fibers during fabrication.

Formulations

Compositions, fibers, membranes, or multiple-layer membranes of the invention of the invention can be conveniently provided as sterile preparations. In one embodiment, a composition of the invention is provided as a liquid, liquid suspension, gel, viscous composition, or solid composition. Liquid, gel, and viscous compositions are somewhat more convenient to administer, especially by injection. Viscous compositions can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the cells (e.g., embryonic stem cells, neuronal progenitors, differentiated neurons) as desired. Such compositions may be in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. In addition, silver salts can be used as thickening agent. See also U.S. Pat. Nos. 8,367,094; 8,173,151; and 7,998,498 (which are incorporated herein by reference). The silver salts may be added to further improve antibacterial effects of the composition. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Glycerin or similar components can be added to the admixture to improve fiber and membrane flexibility.

Exemplary agents that may be delivered together with a composition, fiber, membrane, or multiple-layer membrane of the invention of the invention include, but are not limited to, antibiotics (including, e.g., antibacterial silver salts), analgesics, anticoagulants, immunosuppressants, the therapeutic substance is selected from the group consisting of anesthetics, hypnotics, sedatives, sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmondics, appetite suppressants, neuroactive substances, neurotransmitter agonists, antagonists, receptor blockers, reuptake modulators, beta-adrenergic blockers, calcium channel blockers, disulfarim, muscle relaxants, analgesics, antipyretics, stimulants, anticholinesterase agents, parasympathomimetic agents, hormones, antithrombotics, thrombolytics, immunoglobulins, hormone agonists, hormone antagonists, vitamins, antineoplastics, antacids, digestants, laxatives, cathartics, antiseptics, diuretics, disinfectants, fungicides, ectoparasiticides, antiparasitics, heavy metals, heavy metal antagonists, chelating agents, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, antioxidants, anti-inflammatories, wound care products, antitumoral agents, antiangiogenic agents, antigenic agents, wound healing agents, plant extracts, growth factors, growth hormones, cytokines, immunoglobulins, emollients, humectants, anti-rejection drugs, spermicides, conditioners, antibacterial agents, antifungal agents, antiviral agents, tranquilizers, cholesterol-reducing drugs, antitussives, histamine-blocking drugs and monoamine oxidase inhibitors. Other agents include proteins such as any one or more of activin A, adrenomedullin, acidic FGF, basic fibroblast growth factor, angiogenin, angiopoietin-1, angiopoietin-2, angiopoietin-3, angiopoietin-4, angiostatin, angiotropin, angiotensin-2, bone morphogenic protein 1, 2, or 3, cadherin, collagen, colony stimulating factor (CSF), endothelial cell-derived growth factor, endoglin, endothelin, endostatin, endothelial cell growth inhibitor, endothelial cell-viability maintaining factor, ephrins, erythropoietin, hepatocyte growth factor, human growth hormone, TNF-alpha, TGF-beta, platelet derived endothelial cell growth factor (PD-ECGF), platelet derived endothelial growth factor (PDGF), insulin-like growth factor-1 or -2 (IGF), interleukin (IL)-1 or 8, FGF-5, fibronectin, granulocyte macrophage colony stimulating factor (GM-CSF), heart derived inhibitor of vascular cell proliferation, IFN-gamma, IFN-gamma, integrin receptor, LIF, leiomyoma-derived growth factor, MCP-1, macrophage-derived growth factor, monocyte-derived growth factor, MMP 2, MMP3, MMP9, neuropilin, neurothelin, nitric oxide donors, nitric oxide synthase (NOS), stem cell factor (SCF), VEGF-A, VEGF-B, VEGF-C, VEGF-D, VEGF-E, VEGF, and VEGF164. Other agents that may be delivered together with a cell of the invention include one or more of LIF, bone morphogenic protein (BMP), retinoic acid, trans-retinoic acid, dexamethasone, insulin, indomethacin, fibronectin and/or 10% fetal bovine serum, or a derivative thereof. Other agents include small oligonucleotides, such as SiDNA or SiRNA including at least a portion of sequences to a therapeutic target.

Those skilled in the art will recognize that the polymeric components of the compositions should be selected to be chemically inert and will not affect the viability or efficacy of the cell as described in the present invention. This will present no problem to those skilled in chemical and pharmaceutical principles, or problems can be readily avoided by reference to standard texts or by simple experiments (not involving undue experimentation), from this disclosure and the documents cited herein.

Dosages

A composition, fiber, or membrane of this invention can be applied or implanted in an amount effective to provide wound-healing or other properties. In certain embodiments, a membrane of the invention provides a barrier effective to prevent infiltration of pathogenic bacteria into the wound site. The skilled artisan can readily determine the amount of the composition, fiber, or membrane of the invention to be administered in methods of the invention. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Delivery Methods

Compositions of the invention (e.g., scaffolds comprising cells) can be provided directly to a tissue or organ of interest, such as a tissue damaged from injury or disease (e.g., by administration into the central or peripheral nervous system). Compositions can be administered to subjects in need thereof by a variety of administration routes. Methods of administration, generally speaking, may be practiced using any mode of administration that is medically acceptable, meaning any mode that produces effective levels of the active compounds without causing clinically unacceptable adverse effects. Such modes of administration include surgical engraftment or injection (e.g., intramuscular, intracardiac, intraocular, intracerebroventricular).

Kits

Compositions, fibers, membranes, or multiple-layer membranes of the invention may be supplied along with additional reagents in a kit. The kits can include instructions for the preparation of a material (such as a membrane), a treatment regime, reagents, and equipment (test tubes, reaction vessels, needles, syringes, etc.). The instructions provided in a kit according to the invention may be directed to suitable operational parameters in the form of a label or a separate insert.

In one embodiment, compositions, fiber, membranes, or multiple-layer membranes of the invention are useful for the treatment or prevention of injury or disease of bone or soft tissue. The present invention provides compositions and methods of treating such injuries or diseases and/or symptoms thereof characterized by the loss of cells, or loss of tissue structure, function or activity. The methods of the invention comprise administering a therapeutically effective amount of a composition, fiber, membrane, or multiple-layer membrane described herein to a subject (e.g., a mammal, such as a human). Thus, one embodiment is a method of treating a subject suffering from or susceptible to a disease, condition or disorder characterized by the loss of cells, or loss of tissue structure, function or activity. The method includes the step of administering to the mammal a therapeutic amount of a characterized by the loss of cells, or loss of tissue structure, function or activity herein sufficient to treat the disease, condition, or disorder, or symptom thereof, under conditions such that the disease, condition, or disorder, or symptom thereof is treated.

The methods herein include administering to the subject (including a subject identified as in need of such treatment) an effective amount of a composition, fiber, membrane, or multiple-layer membrane described herein, to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compositions herein, such as a composition, fiber, membrane, or multiple-layer membrane described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Preparation of Fibers and Membranes

The purpose of this study was to engineer a membrane with antibacterial and regenerative properties that degrades within 6-12 weeks allowing for retention of the graft while promoting a more rapid closure of the overlying tissue. To achieve this, electrospun gelatin+chitin whiskers (CW)+honey membranes were fabricated and subsequently compressed. Compressed membranes have increased handleability, are less porous, and maintain non-compressed fiber diameter. Less porous scaffolds are desired for this application to provide guided regeneration for tissue closure. Furthermore, it is documented that larger fibers and the addition of honey (antimicrobial by nature) can independently enhance the pro-regeneration response. Chitin whiskers (CW) are an emerging, novel filler, and have been shown to reinforce both synthetic and natural polymeric structures. The good biocompatibility and biodegradability also make it one of the most promising fillers.

In some experiments, gelatin was dissolved in 1,1,1,3,3,3-hexafluoro-2-propanol (HFP) or 9:1 acetic acid:deionized (DI) water and electrospun with MEDIHONEY® or MANUKAGARD® (0-50 wt. %). Electrospinning using HFP or acetic acid:DI water as a solvent resulted in scaffolds with micron- and nano-sized fibers, respectively. Membranes (crosslinked and non-crosslinked with 25 mM 1-Ethyl-3-(3-dimethylaminopropyl)carbodiimide) were compressed (one or multiple layers) using a hydraulic press. Compressed membranes have increased handleability, are less porous, and maintain non-compressed fiber diameter. Less porous scaffolds are desired for this application to provide guided regeneration for tissue closure. Furthermore, it is documented that larger fibers and the addition of honey (antimicrobial by nature) can independently enhance the pro-regeneration response. This study will further analyze the regenerative response of human dermal fibroblasts seeded on composite membranes.

Materials and Methods

CWs were prepared according to Dufresne's method with minor modification (Ji, Y-L, et al. *Carbohydrate Polymers*, 87, 2313-2319, 2012). The desired amount of CWs (15 wt % of gelatin) were redispersed in 2,2,2-trifluoroethanol (TFE) by ultrasonication. Gelatin (Type B) was added to the CW solution at 140 mg/mL. MEDIHONEY® (100% Active Leptospermum Honey) was then added to the gelatin+CW solution at 0, 5, 10 wt % of gelatin. Solutions were mixed and incubated at 37° C. overnight to ensure the complete dissolving/mixing of all components. Solutions were loaded into a 5 mL syringe and electrospun using the following parameters: 5 mL/hr, +22 kV, and 5 inch air gap distance. Fibers were collected on a 1 inch (diameter) rotating grounded stainless steel mandrel.

Scaffolds were compressed to create multilayer membranes with improved mechanical integrity while maintaining the fibrous nanostructure. 4 layers of the same scaffold were compressed using metal platens on a hydraulic press for 30 seconds at 4500 pounds. Non-compressed and compressed samples of each scaffold (0, 5, 10 wt % honey) were imaged using a scanning electron microscope (SEM) at +20 kV to observe fiber diameter and general porosity. Fiber diameter of all non-crosslinked scaffold types, both compressed and non-compressed, was further analyzed by calculating average fiber diameters and standard deviations using FibraQuant™ 1.3 software (nanoScaffold Technologies, LLC).

Crosslinking of all 4-layered membranes was achieved by placing each membrane in a medium petri dish containing 40 mM 1-Ethyl-3-(3-dimethylaminopropyl)carbodiimide) (EDC) in ethanol for 21 hours at room temperature. Upon completion, the membranes were immersed in ethanol and 6 mm discs were punched and used in cell studies.

Dog-bone punches (2.71 mm wide at narrowest point with a length of 18.63 mm) were used for mechanical testing. Uniaxial tensile testing was performed on the dog-bone samples (n=3) with a 100 N load cell, extension rate of 1 mm/s, and a 7.7 mm starting distance between grips. Modulus of elasticity and strain at break were calculated from the stress-strain output.

Clinical adaptability/formability of membranes was scored by an oral surgeon under both dry and hydrated (0.9% NaCl for 30 minutes) conditions. COLLAPLUG® collagen membrane (Zimmer Dental) was used as a control since it is currently one of the membrane barrier standards for socket preservation surgery.

Cell Viability (DAPI)

6 mm punches of the compressed membranes were disinfected directly following crosslinking via a 30 minute ethanol soak followed by three 10 minute PBS washes. Human dermal fibroblasts (HDFs) were seeded on the scaffold punches (n=3) at 5,000 cells/well in a 96 well plate. Studies were completed over 7 days with time points at 1, 3, and 7 days. Media changes occurred at every time point. After each time point, cellularized scaffolds were fixed in 10% buffered formalin. 4',6-diamidino-2-phenylindole (DAPI) cell nuclei staining was then performed. Scaffolds were imaged using an Olympus fluorescent microscope to visualize viable cells.

Results, Discussion and Conclusion

SEM images of non-compressed and compressed electrospun gelatin+15% CW+honey scaffolds (non-crosslinked) are shown in FIG. 1. Fiber size distributions are shown in FIG. 2. FIGS. 3A and 3B show the strain at break (3A) and modulus of elasticity (3B) measurements.

Adaptability/Formability

Table 1 shows the assessment of clinical adaptability of dry and hydrated membranes having varying amounts of honey. Best membrane (wet): 0% and 10% honey. Worst membrane (wet): CollaPlug control (does not hold shape, difficult to adapt). Clinical significance: compressed membrane needs to be hydrated before use. Formability can be tailored by compressing fewer or more layers (FIGS. 4A-4B).

TABLE 1

Clinical adaptability of dry (D) and hydrated (wet, W) compressed membranes and CollaPlug controls scored by an oral surgeon (top).

|  | 0 | 1 | 2 | 3 | 4 |
|---|---|---|---|---|---|
| 0% Honey |  | D |  |  | W |
| 5% Honey |  | W | D |  |  |
| 10% Honey | D |  |  |  | W |
| CollaPlug | W |  |  |  | D |

Scale
0 = cannot be formed, either brittle or tears apart
4 = can easily be formed, maintains structure when handled Electrospinning and Compression FIG. 5 shows images of compressed electrospun membranes. Compression while maintaining fibrous architecture and dimensions was achieved. Some fiber welding was noticed post-compression which is most likely dependent on the crystallization state of the honey. A more dehydrated scaffold (in desiccator) will result in a more crystalline honey structure and ultimately, less non-welded fibers upon compression.

Mechanical Testing

All scaffolds failed between 90-120% strain (no significant difference). Scaffolds containing 10% honey had significantly higher modulus values compared to 0% honey. This was unexpected at first since intuitively, more honey would cause the scaffolds to be less rigid. It was hypothesized since the mechanical testing was performed directly from ethanol that the honey was in a dehydrated (more crystalline) state, which caused the increase in modulus. Future work will incorporate glycerin and analysis of samples hydrated with PBS which will most likely induce a less crystalline honey architecture and result in less stiff scaffolds.

Cell Viability

Viable cells (HDFs) were visible on the surface of every scaffold for each time point. Visually, it is difficult to determine any differences. However, future studies will analyze cell proliferation and cell secreted regenerative markers and extracellular matrix.

Example 2

Preparation of Sponge

Sponges were fabricated using a 30 mg/mL gelatin solution in deionized water and heated to 37° C. to ensure all gelatin was in solution. 10% CW (chitin whisker) was added to the gelatin solution and sonicated. 0-30 mg/mL honey was then added to the gelatin+CW solution. After the honey went into solution, 25 mM 1-Ethyl-3-(3-dimethylaminopropyl)carbodiimide) (EDC) was added to the gelatin+CW+Honey solution, immediately transferred to a cylindrical mold, frozen at −80° C., and lyophilized. Dry sponges were compressed at 4,500 pounds for 30 seconds using a hydraulic press.

FIGS. 6A-6B DinoLite images of general gross appearance of non-compressed and compressed gelatin+10% CW+30 mg/mL honey sponges. Noncompressed: 5.5 mm thickness; compressed: 0.3 mm thickness.

Sponges can be manufactured at any size (depending on the mold) and subsequently compressed.

Particulate is formed similarly to the lyophilized membrane with on additional step (FIGS. 7A-7B). The particulate can be used in combination with the lyophilized membrane, as shown in FIG. 7C. After the composite solution is frozen, the frozen material can be ground up (e.g. using a blender) to form something similar to "crushed ice". This crushed ice is then lyophilized overnight to form the particulate. Since the particulate is intended for bone regeneration, the concentration of filler (e.g. hydroxyapatite) will be increased (e.g. to 50% or more) to enhance osteoconductivity. Development and refinement of particulate can consist of optimizing the manufacturing process to obtain fairly consistent particle size. This can be achieved by controlling the blending of the frozen composite to achieve the crushed ice or by cryopulverizing (in liquid nitrogen) larger lyophilized pieces into smaller. Particle sizes can be filtered by size using sieves or equivalent technology to obtain uniform/defined particulate sizes. Multiple methods of achieving (lyophilizing the "crushed ice" versus cryopulverizing larger (mm-sized) particulate) particle size can be performed in order to optimize particulate size. Preferably, the particulate has a size or an average diameter ranging from about 100 μm to about 10 mm, or particularly from about 1 mm to about 5 mm.

Both dry and hydrated, compressed membranes of this composition should be hydrated before use (FIG. 7E) and can be easily cut/sized with scissors and have great handleability. Upon hydration, membranes become more flexible and can be maneuvered within the surgery site easily upon implantation. Once initially hydrated, the handleability alone is a significant improvement from existing membranes such as COLLAPLUG®. Even after a few days of being hydrated, current natural biodegradable membranes such as BIO-GIDE® begin to lose their mechanical integrity.

Example 3

Compressed Membrane for Bone Grafting Applications

Further, the excellent biocompatibility and biodegradability also make it one of the most promising fillers. These compressed membranes combine the advantages of a film-like material with a bioactive surface to further enhance cell response and guided tissue regeneration (GTR). Gelatin+CW+MH membranes exhibit enhanced biocompatibility and biodegradability which suggests their use as an alternative to current clinical products.

Methods and Materials
Scaffold Fabrication

Scaffolds were fabricated using a 30 mg/mL gelatin solution. 10% CW (wt % of gelatin) were dispersed in DI water and sonicated using a microtip for 30 seconds at 2% amplitude. Gelatin and 0, 5, or 25% MH (wt % of gelatin) were then solubilized within the CW solution via incubation at 37° C. for 1 hour. After a uniform solution was achieved, 40 mM 1-Ethyl-3-(3-dimethylaminopropyl)carbodiimide) EDC cross-linker was added, briefly mixed, immediately transferred to a small Petri dish, frozen overnight at −80° C., and lyophilized Lyophilized sponges were then sliced into 4 mm thick sections and compressed using a hydraulic press (FIG. 8) at 4500 pounds for 30 seconds to create the final membranes (thickness between 300-400 μm).

Degradation

Scaffold degradation via release kinetics was studied by quantifying protein release from each 6 mm scaffold over 14 days. Scaffolds were incubated at 37° C. in 1×PBS with PBS replaced at each time point. After 1, 4, 7, 11, and 14 days, the releasate was analyzed for general protein using the Pierce BCA Protein Assay. Gelatin and MH could not be distinguished and both contributed to the quantitative cumulative mean concentration results. To account for this, cumulative percent release was calculated by using fully degraded non-crosslinked scaffolds as total initial protein content: % release=(release)/(total initial content)*100.

Cell Adhesion 6 mm discs of each scaffold type were loaded into 96-well plates. Current clinical membranes, GEISTLICH BIO-GIDE® (collagen) and KLS MARTIN RESORB-X® (polylactic acid, PLA film), were punched and used as clinical controls. All membranes were disinfected (30 minutes Ethanol and three 10 minute PBS washes) prior to cell seeding. 20,000 human dermal fibroblasts (HDFs) were seeded on membranes and cultured for 14 days. After 1, 7, and 14 days, media was removed and frozen while cellularized membranes were fixed in 10% formalin. Fixed scaffolds were stained with 4'-6-diamidino-2-phenylindole (DAPI) and their cell seeded surfaces fluorescently imaged to visualize cell attachment.

Mechanical Testing

Hydrated acellular scaffolds were analyzed using a uniaxial platen compression system to determine peak load. Rectangles (2.5×0.5 cm) were cut and fixed in an arch position by anchoring the ends 1 cm apart (FIGS. 9A-9C). The upper platen was lowered to the scaffold surface and the following parameters were used: 10 mm/min test speed and 250 samples/second data acquisition rate. Compression was continuous until the top platen reached the anchors. Run was terminated just before this contact occurred and maximum force exerted by the scaffolds was recorded in Newtons (N).

Clinical Adaptability/Formability

After hydration, all gelatin+CW+MH membranes were scored by an oral surgeon under both dry and hydrated (0.9% NaCl for 30 minutes) conditions. KLS MARTIN, BIO-GIDE and COLLAPLUG® (collagen membrane, Zimmer Dental) were used as clinical control membranes.

Discussion and Conclusion
Sponges and Compression

All gelatin+CW+MH scaffolds exhibited the same non-compressed (porous) and compressed (less porous) surface architecture with no visual discernible differences between scaffold types (FIG. 10). The compressed surface provides a template for GTR compared to a porous membrane where cells initially migrate throughout the scaffold.

Degradation

The addition of 5% MH resulted in a similar concentration release profile compared to 0% MH, with both beginning to plateau after 14 days (FIGS. 11A-11B). The +25% MH membranes exhibited a more linear release profile over 14 days, suggesting degradation at a constant rate. After 1 day, 0%, +5%, and +25% MH released 17%, 17%, and 22% of total initial content, respectively. After 14 days, 0%, +5%, and plus 25% MH released 44%, 34%, and 49% of total initial content, respectively. The cumulative percent release graphs revealed interesting profiles, suggesting the addition of 5% MH slows the degradation rate of the scaffold. This was not expected since the addition of any amount of MH was thought to increase the degradation rate (evident in +25% MH graph). The data provides insight to the tailorable degradation rates solely based on the incorporation of various concentrations of MH.

Adaptability/Formability

Clinical adaptability of dry (D) and hydrated (wet, W) compressed membranes and Bio-Gide, KLS Martin, and CollaPlug controls scored by an oral surgeon. When hydrated, all gelatin+CW+MH membranes handled similarly to Bio-Gide controls with higher percentages of incorporated MH resulting in increased membrane tearing (Table 2). However, dry gelatin+CW+MH membranes had greater adaptability compared to controls. In the hands of the surgeon, compressed membranes handled similar to clinical collagen membranes (FIGS. 13A-13C).

TABLE 2

Adaptability/Formability

| | 1 | 2 | 3 | 4 | 5 |
|---|---|---|---|---|---|
| 0% MH | | | W | | D |
| +5% MH | | W | | | D |
| +25% MH | | W | | | D |
| Bio-Gide | | W | D | | |
| KLS Martin | | D | | W | |
| CollaPlug | W | | | | D |

Scale
1 = cannot be formed, brittle or tears apart
2 = can easily be formed, maintains structure when handled Compression Testing All gelatin+CW+MH membranes exerted a max force within the range of 0.02-0.03 N while the Bio-Gide and KLS Martin controls exerted 0 N and 0.75 N, respectively. Gelatin+CW+MH membranes show improved mechanical properties compared to the Bio-Gide control which would not maintain an arch for testing (Table 3). The higher KLS Martin values are expected since it is a non-porous PLA film.

TABLE 3

Compression Testing

| 0% MH | +5% MH | +25% MH | Bio-Gide | KLS Martin |
|---|---|---|---|---|
| 0.03 N | 0.03 N | 0.02 N | 0 N | 0.75 N |

Cell Adhesion

The addition of MH significantly increased cell attachment on day 1 compared to 0% MH and Bio-Gide membranes (FIG. 12). KLS Martin membranes also attached a high number of cells because of its 2D film surface similar to tissue culture plastic. The drawback of KLS Martin (PLA) is its degradation which leads to an acidic microenvironment. After 7 and 14 days, all gelatin+CW+MH membranes were covered in cells where Bio-Gide controls still had no visible cells attached. Fluorescent imaging became more difficult at 7 and 14 days most likely due to some migration of the cells as they remodeled the membrane. Future studies will analyze cell proliferation, viability, secreted regenerative markers, and extracellular matrix production.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A composition comprising:
   a) 100 parts by weight of a biodegradable polymer comprising gelatin or collagen,
   b) honey in an amount of 15 to 100 parts by weight relative to the 100 parts by weight of the polymer, wherein the honey has a Unique Manuka Factor rating of at least 10; and
   c) hydroxyapatite present in an amount of 5 to 20 parts by weight relative to the 100 parts by weight of the polymer, wherein the composition promotes regeneration of soft tissue in a subject when the composition is contacted with the soft tissue,
   wherein the composition is degradable in vivo, and
   wherein the composition is a solid and is configured for implantation in a subject.

2. The composition of claim 1, wherein the biodegradable polymer comprises an additional protein.

3. The composition of claim 1, wherein the biodegradable polymer comprises gelatin.

4. The composition of claim 1, wherein the biodegradable polymer comprises collagen.

5. The composition of any of claims 1 or 2 through 4, wherein the biodegradable polymer comprises poly(lactic acid), polydioxanone (PDO) or a blend thereof with gelatin or collagen.

6. The composition of claim 1 further comprising at least one additional filler or at least one additional antibiotic.

7. The composition of claim 1, wherein the composition is lyophilized.

8. The composition of claim 1, wherein the hydroxyapatite has an average diameter of from 1 nm to 10 μm.

9. The composition of claim 1, wherein the hydroxyapatite has an average diameter of from 200 nm to 2 μm.

10. A method of promoting soft tissue healing in a damaged tissue, the method comprising contacting the damaged tissue with the composition of claim 1.

* * * * *